US005395351A

United States Patent [19]

Munsch

[11] Patent Number: 5,395,351

[45] Date of Patent: Mar. 7, 1995

[54] SELF-VALVING CONNECTOR AND INTERFACE SYSTEM AND A METHOD OF USING SAME

[75] Inventor: John M. Munsch, Libertyville, Ill.

[73] Assignee: Baxter International Inc., Deerfield, Ill.

[21] Appl. No.: 128,630

[22] Filed: Sep. 29, 1993

[51] Int. Cl.[6] ................................ A61M 5/00

[52] U.S. Cl. ................................ 604/256; 604/167; 604/283; 604/905; 215/355

[58] Field of Search .................. 604/30, 91, 167, 245, 604/254, 256, 283, 320, 321, 323, 326, 335, 350, 905

[56] References Cited

U.S. PATENT DOCUMENTS 2,687,731 8/1954 Larussi et al. ...................... 604/256

*Primary Examiner*—C. Fred Rosenbaum
*Assistant Examiner*—Perry E. Van Over
*Attorney, Agent, or Firm*—Thomas S. Borecki; Charles R. Mattenson; Robert M. Barrett

[57] ABSTRACT

A connector having an occluder which transposes between a first position and a second position is provided for maintaining a sterile environment during connection and disconnection of fluid communication between a container and a fluid line. The occluder is in the form of a spherical ball integrally formed with a length of tubing. The occluder has a diameter slightly larger than an end of the connector such that the occluder rolls into the end upon disconnecting from the system. An interface may be provided to receive a single connector or a pair of connectors to assist in fluid control between the container and the fluid line.

19 Claims, 5 Drawing Sheets

SELF-VALVING CONNECTOR AND INTERFACE SYSTEM AND A METHOD OF USING SAME

BACKGROUND OF THE INVENTION

The present invention generally relates to connectors. More specifically, the invention relates to a system having a connector and an interface in a system for delivery of a solution wherein the connector automatically closes upon disconnecting.

In a variety of industries, and for a variety of applications, it is necessary to create and provide a flow path. In many situations, most specifically in the medical industry, it is necessary to create sterile fluid flow paths.

It is, of course, generally known to provide fluid delivery to a patient for a variety of purposes, such as delivery of a medicament, provide nutrition, and peritoneal dialysis and the like. Such fluid delivery necessitates in many instances the creation of sterile flow paths. Some such procedures require the sterile flow paths to be disconnected and reconnected.

For example, it is known to use a cannula or a needle to inject into a patient a solution through the use of a length of tubing which is further connected to a container housing the solution. Often, an adaptor or other connector is provided for enabling fluid communication between the container and the patient through the tubing. For example, a connector may be provided at a port on the container to connect an end of the length of tubing to the container.

It is also well known to provide solutions to patients, such as for peritoneal dialysis. In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. The proper acid-base electrolyte and fluid balance to be returned to the blood is achieved, and the dialysis solution is simply drained from the body cavity through the catheter.

This procedure is generally repeated three or four times daily for such a patient. Therefore, repeated connections and disconnections are required to be made from the system. Further, such a patient is often interrupted during administration of solution into the body requiring disconnection from the system.

At least three issues arise with respect to the disconnection and reconnection of a sterile flow path such as that used for peritoneal dialysis. One requirement is that the system must provide a quick and simple disconnection from the system. It is also required that a sterile, contaminant-free environment be maintained after disconnection. Further, the system must provide means for a simple reconnection to the system.

If dismantling of the entire setup is required, a patient generally will not permit the interruption and will continue receiving the solution ignoring the interruption. On the other hand, if the disconnection and/or reconnection cannot be performed without contaminating the system, the contaminated system components or the entire system must be replaced. In the alternative, the contaminated components of the system must be sterilized before reuse of the system. Again, therefore, the patient will ignore the interruption and continue with the administration of solution from the system.

At times, however, interruptions, such as emergencies, will require disconnection from the system. Therefore, a need exists for an improved system for simplifying disconnection and reconnection without contamination of the components of the system.

SUMMARY OF THE INVENTION

The present invention provides a connector and an interface to allow for the disconnection and reconnection of fluid flow through a sterile fluid path, for example, through a length of tubing between a fluid source and a destination, such as a fluid line or a patient. An occluder is provided to selectively open and close an opening of the tubing. As a result, potentially contaminated surfaces are sealed from entering the interior of the tubing.

To this end, in an embodiment of the present invention, a connector is provided for controlling fluid communication in a fluid path between a first fluid line and a second fluid line. The connector comprises a flange and a tube, defining in part the first fluid line, having an interior surface and an exterior surface wherein the tube extends from the flange and is located so as to expose a portion of the interior surface of the tube by a portion of the tube being folded over a portion of the flange. An occluder is coupled to the interior surface of the tube wherein the occluder is so constructed and arranged to transpose between a first position and a second position in response to movement of the flange.

In an embodiment, the tube and the occluder are integrally formed.

In an embodiment, the flange has a first and a second end wherein the first end has a larger exterior diameter than the second end.

In an embodiment, the occluder is spherically shaped.

In an embodiment, the occluder has a diameter larger than the cross-sectional diameter of the interior surface of the tube.

In another embodiment of the present invention, a system is provided for controlling fluid communication between a first fluid line and a second fluid line. The system comprises a first tubing, defining at least in part the first fluid line, having an interior surface and an exterior surface. A first connector receives the first tubing and allows the first tubing to be coupled to the second fluid line wherein a portion of the first tubing folds over the first connector exposing a portion of the interior surface of the first tubing. A first occluder is coupled to the interior surface of the first tubing, the first occluder being so constructed and arranged to selectively transpose between a first position and a second position, in the first position the occluder covers an opening of the first tubing and in a second position the occluder does not cover the opening of the first tubing. A means for assisting transposes the first occluder between the first position and the second position.

In an embodiment, a flange is provided within the first tubing for receiving the means for assisting. The occluder moves to the first position when the flange is removed and to the second position when the flange is received in the means for assisting.

In an embodiment, the means for assisting transposes the occluder from the second position to the first position within an enclosure integrally formed with the means for assisting.

In an embodiment, a second tubing is provided defining in part the second fluid line having an interior surface and an exterior surface. A second connector receives a portion of the second tubing wherein a portion of the second tubing is folded over the second connector exposing a portion of the interior surface of the second tubing. A second occluder is coupled to the interior surface of the second tubing wherein the second occluder is so constructed and arranged to selectively transpose between a first position and a second position.

In an embodiment, the first connector and the second connector are moved away from each other, fluid communication from the two lines is disconnected, and the occluders automatically move to the first position. In an embodiment, at least one of the connectors can be disconnected from the interface such that its respective occluder transposes into its first position.

In another embodiment of the present invention, a method is provided for controlling fluid flow between a first fluid line and a second fluid line. The method comprises the steps of providing a connector intermediate the first fluid line and the second fluid line; providing a first length of tubing, defining in part the first fluid line, having an interior through the connector; folding a portion of the tubing over the connector exposing a portion of the interior of the tubing; providing an occluder coupled to the interior of the first length of tubing and so constructed and arranged to transpose between a first position and a second position wherein the first position prevents fluid flow through an opening of the tubing and the second position permits fluid flow through the opening in the tubing; and providing means for causing the occluder to move from the first position to the second position.

In an embodiment, the method further comprises the steps of providing an enclosure for moving the occluder and interrupting fluid flow.

In an embodiment, the method further comprises the step of removing the connector from the enclosure such that the occluder transposes to the first position.

It is, therefore, an advantage of the present invention to provide a simple and quick disconnect of a fluid source and a fluid line.

Another advantage of the present invention is to provide a connector for automatically stopping fluid flow by disconnecting of the connector.

Yet another advantage of the present invention is to provide a system and a method which prevents contamination of the fluid line during connecting, disconnecting and reconnecting thereof.

A further advantage of the present invention is to provide a system and a method having an interface for connecting a first length of tubing to a second length of tubing.

A still further advantage of the present invention is to provide a system and a method having an interface for interrupting fluid flow without detaching one or more lengths of tubing from the interface.

Moreover, an advantage of the present invention is to provide a system and a method for simple and repeated interruption of fluid communication between a fluid source and a destination, such as a patient.

Further, an advantage of the present invention is to provide a system and a method for controlling of fluid communication between a container and a patient by the patient.

Additional features and advantages of the present invention are described in and will be apparent from the detailed description of the presently preferred embodiments and from the drawings.

DETAILED DESCRIPTION OF THE PRESENTLY PREFERRED EMBODIMENTS

The present invention provides a system and a method for controlling flow of a fluid between a source and a fluid line which may be coupled to a destination, such as a patient. More specifically, the present invention provides a system and a method for providing means for establishing fluid flow in a sterile system and allowing disconnecting of the sterile fluid flow and reconnection in a manner which effectively avoids contamination of the system.

To this end, the system provides one or more connectors along with an interface. The system can be simply and quickly disconnected to interrupt fluid flow through the system. Further, the system can be simply reconnected following disconnection without contamination to the system. The connector, interface and method may be implemented in any system in which a fluid or a solution is delivered from a source to a destination. However, by way of illustration, embodiments of the invention will be described hereinafter with respect to solution delivery from a container to a patient, such as for peritoneal dialysis.

Figure 1:
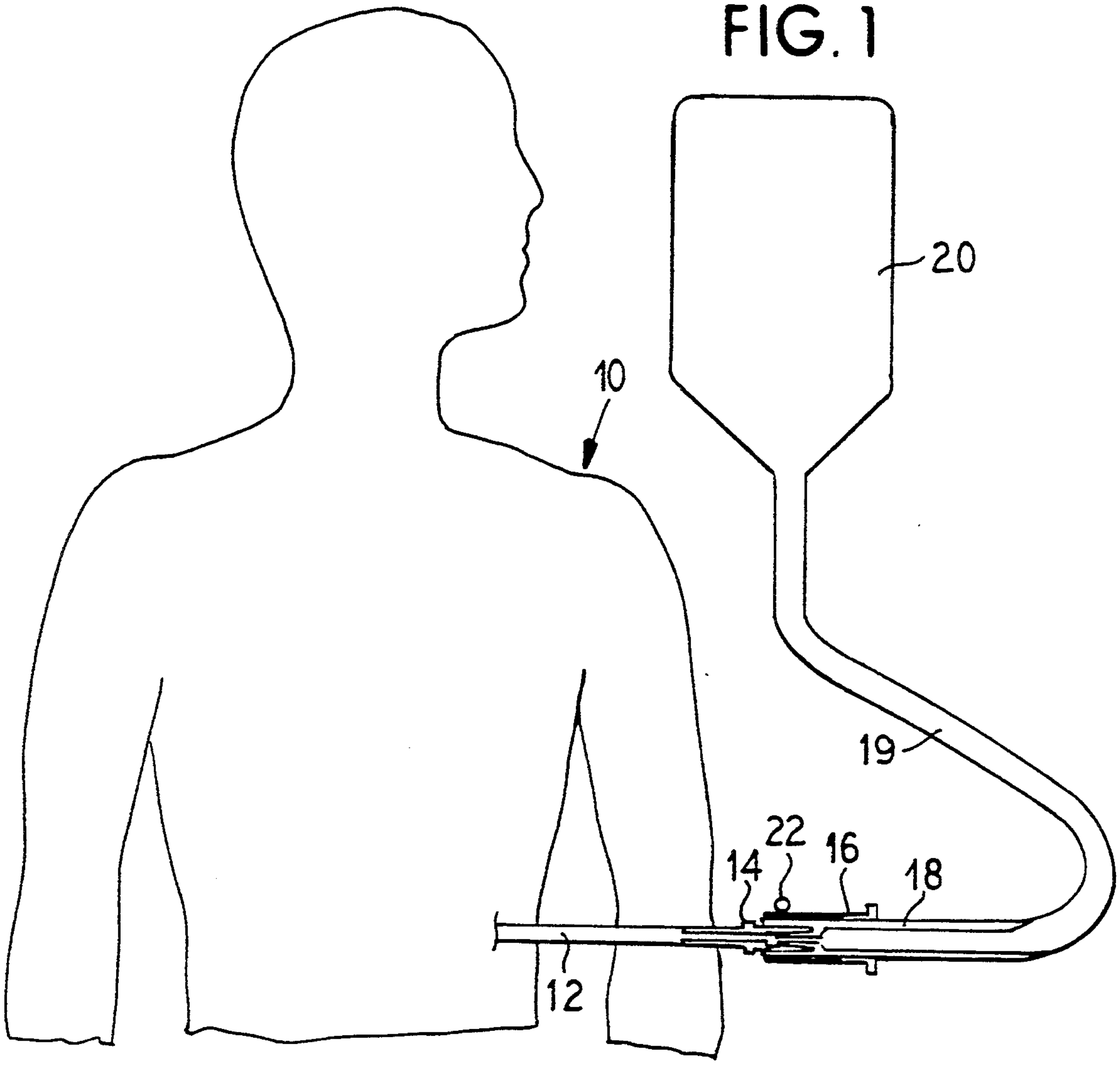
FIG. 1 illustrates a perspective view of a connector and an interface of the present invention in a fluid line for interrupting fluid flow between a patient and a fluid source.

Referring now to the drawings, FIG. 1 generally illustrates a user or a patient 10 receiving, for example, a first length of tubing 12 into a peritoneal cavity for peritoneal dialysis. The first length of tubing 12 at one end connects to a catheter (not shown) for allowing fluid flow into the patient 10. At an opposite end, the first length of tubing connects 12 to an interface generally shown, in one embodiment, at 14. An opposite end of the interface 14 connects to a connector 16 which will be further described in detail hereinafter.

A second length of tubing 19 is provided for fluid communication between the connector 16, and specifically an interface 18, and a container 20. The interface 18 may be a separately formed member connected to the tubing 19. In the alternative, the interface 18 may be an integrally formed extension of the second length of tubing 19. When the connector 16 is in the position shown in FIG. 1, i.e. the non-occluded position, a solution or the like may be delivered from the container 20 to the patient 10. The open position is indicated by an occluder or ball 22 integrally formed with the connector 16 in a position outside of the connector 16 as shown in FIG. 1.

Figure 2:
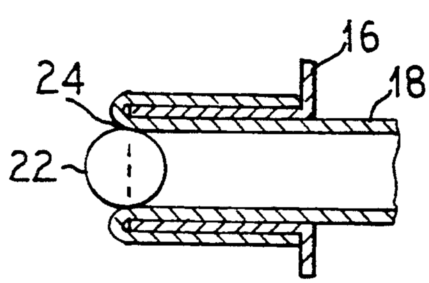
FIG. 2 illustrates a cross-sectional view of a connector of the present invention in an occluded position.
Figure 3:
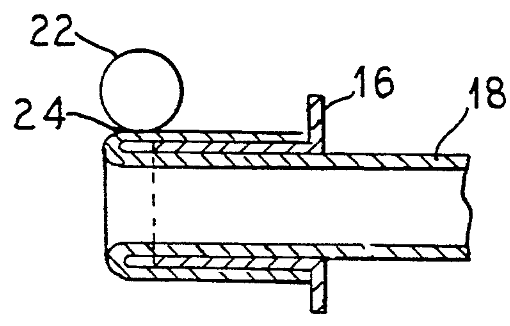
FIG. 3 illustrates a cross-sectional view of a connector of the present invention in a non-occluded position.

Referring now to FIGS. 2 and 3, the connector 16 is shown in a closed or occluded position in FIG. 2 and an open or non-occluded position in FIG. 3. The portion of the ball 22 on the exterior of the interface 18 within the connector 16 is potentially subjected to contamination. The other surfaces of the connector 16 are free from contamination due to the operation of the connector 16 in the fluid line to be described hereinafter.

As illustrated in FIG. 2, the ball 22 is integrally formed with an interior wall of the length of interface 18. To this end, the ball 22 is attached to an inside bore of the interface 18 at a point of connection generally designated at 24. The ball 22 has a diameter slightly larger than an inside bore of the interface 18 substantially defined by an interior wall of the connector 16. The interface 18 extends beyond the opening bore of the connector 16 such that an exterior wall of the interface 18 folds over an exterior wall of the connector 16 at an end opposite the end which the interface 18 enters the connector 16.

Therefore, the connecting point 24 of the ball 22 is at a point on the interior wall of the interface 18 substantially at the point which the interface 18 folds over the connector 16. The interface 18 may be an elastomeric-type material, such as silicone, or any other suitable material capable of creating a seal and moving between a first position and a second position. The ball 22, likewise, being integrally formed with the interface 18, is, therefore, also an elastomeric material, such as silicone. The ball 22, as illustrated, is spherically shaped, but may be any shape which secures in the end of the connector 22 forming a sealed relationship preventing fluid flow when in the occluded position.

FIG. 3 illustrates the connector 16 with the ball 22 in a non-occluded or open position. The non-occluded position illustrated in FIG. 3 is achieved by the ball 22 rolling outside of the interface 18. To this end, the patient 10 or other individual may force the connector 16 in a retracted position forcing the interface 18 in a direction opposite that of the connector 16. The ball 22, as a result, since it is attached to the interface 18 moves with the interface 18 to the non-occluded position shown in FIG. 3. As a result, the inside of the interface 18 is exposed through the connector 16.

Upon retraction of the connector 16, the ball 22 rolls out of the bore around the end of the connector 16. To assist in retraction, one end of the connector 16 has a larger exterior diameter than the interior diameter of the connector 16. The exterior diameter at the opposite end is only slightly larger than the interior diameter. The ball 22, therefore, as in the position shown in FIG. 3, is outside of the interface 18 on the exterior side of the connector 16 following retraction thereof by the patient 10 or other individual. As a result, the potentially contaminated surfaces, that is, those portions of the ball 22 outside of the interface 18 as well as the surrounding tubing outside the connector 16, as shown in FIGS. 2 and 3, are transposed or rotated away from the bore of the connector 16. Only the non-contaminated, previously sealed portions, including the bore of the interface 18 and the connector 16, are thereby exposed to the solution.

Referring now to FIGS. 4, 5A, 5B, 6A, 6B and 7A–7C, various embodiments of interfaces for use with the connector 16 are illustrated. The interfaces may assist in effecting movement of the ball 22 between the occluded position and the non-occluded position. To this end, the patient or other individual inserting, adjusting or removing the interface causes the interface to retract the connector 16 forcing the ball 22 into a non-occluded position. In the alternative, the connector 16 may be withdrawn forcing the ball 22 and the connector 16 into the occluded position.

Figure 4:
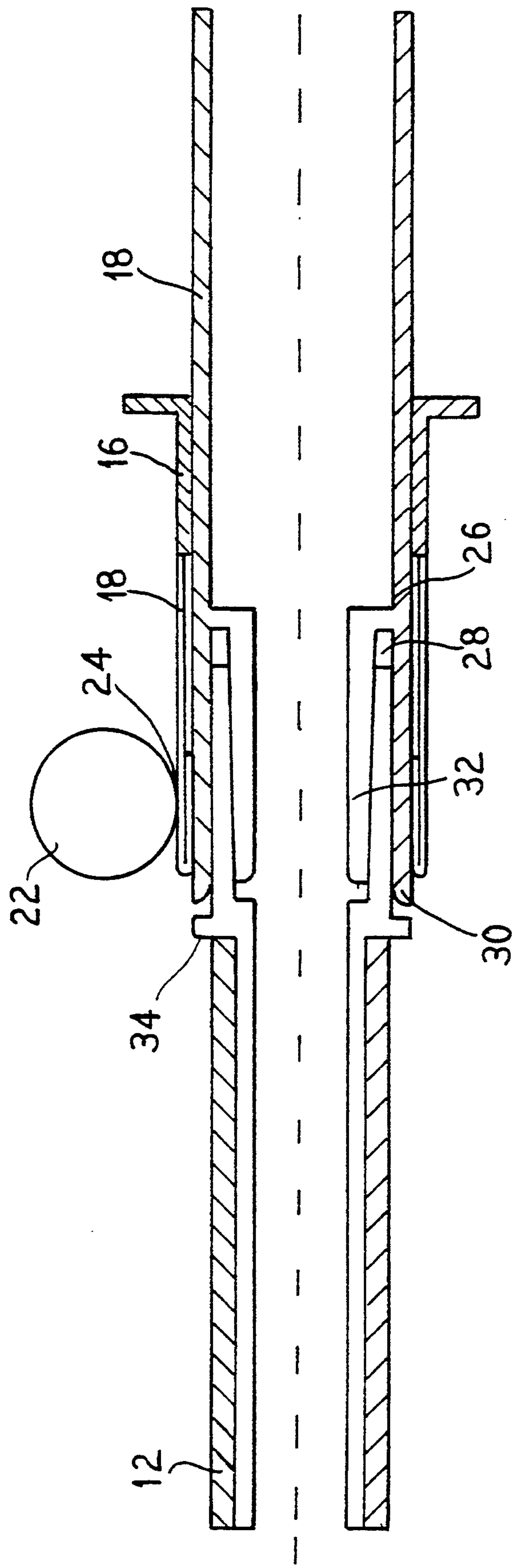
FIG. 4 illustrates a cross-sectional view of a connector and an interface between two lengths of tubing in an embodiment of the present invention.

FIG. 4 illustrates the non-occluded position of the ball 22 wherein the ball 22 is integrally formed with an interior wall of a length of tubing 18′ and is attached at the connecting point 24. The length of tubing 18′ may be formed to extend from the connector 16 as shown or may be integrally formed with the interface 18 which extends from a port of a source, such as the container 20 of FIG. 1. A first interface component 26 has a recess 28 between an exterior wall 30 of the interface 18 and a separately formed interior wall 32. The first interface component 26 is constructed and arranged to receive a second interface component 34 within the recess 28 formed by the first interface component 26.

When the second interface component 34 engages with the recess 28 of the first interface component 26, the ball 22 is in the position shown in FIG. 4 allowing flow of a fluid or solution from a source to a destination, such as a fluid line to a patient. The first interface component 26 is integrally formed with or connected to a length of tubing 18 extending from the patient or the solution bag.

Conversely, the second interface component 34 has a length of tubing 12 extending from the container or the patient opposite from the interface 18. The interface 18 is within the connector 16 and forms the exterior wall 30 of the first interface component 26. A frictional fitting is provided between the first interface component 26 and the second interface component 34. When the first interface component 26 is separated from the second interface component 34, the tubing 18′ integrally formed with the ball 22 seals the opening from the connector 16. An occluded position results when the ball 22 retracts into the open end of the connector 16 or seals the end of the first interface component 26 as shown in FIG. 3, such as when a patient disconnects the second interface component 34 from the first interface component 26.

Figure 5A:
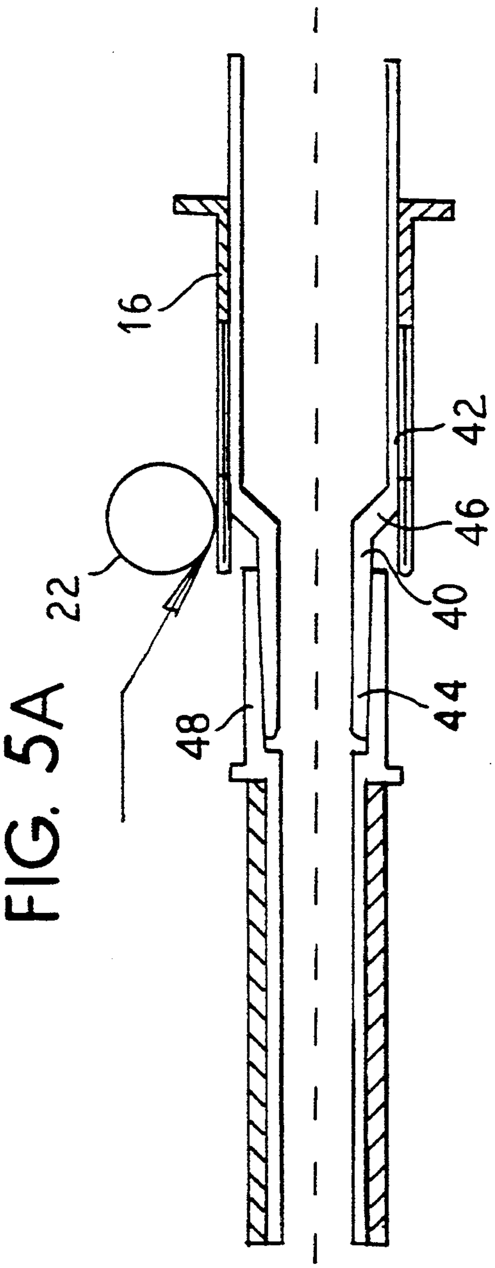
FIG. 5A illustrates a cross-sectional view of a connector and an interface in another embodiment of the present invention in a non-occluded position.
Figure 5B:
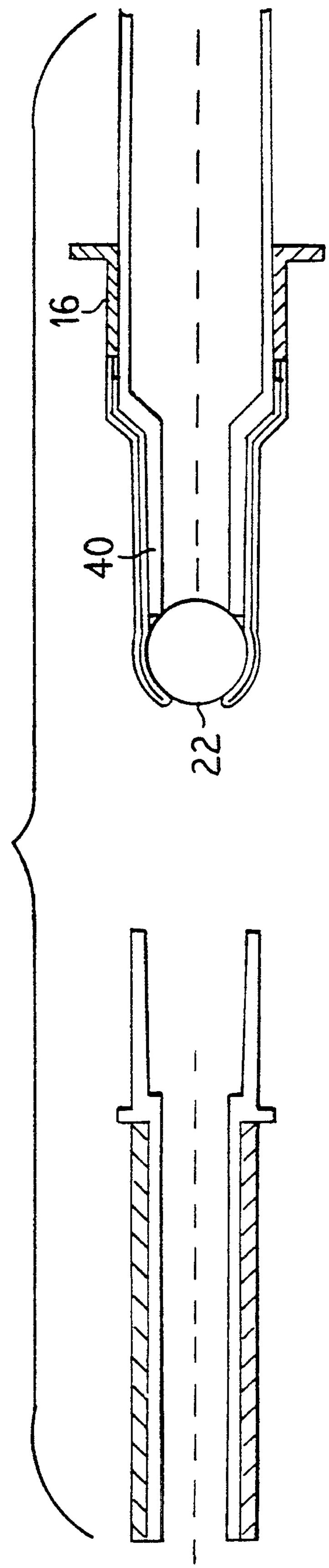
FIG. 5B illustrates a cross-sectional view of a connector and an interface in the embodiment of the present invention as shown in FIG. 5A, but in the occluded position.

FIGS. 5A and 5B illustrate another embodiment of the connector 16 of the present invention and an interface. A first interface component 40 has a tapering diameter from its outermost exterior wall 42 to an exterior wall 44 by a tapering section 46. The first interface component 40 mates with a second interface component 48. To this end, the exterior wall 44 of the first interface component 40 frictionally engages the interior wall of the second interface component 48. The walls provide a sealed relationship from the engagement of the first interface component 40 with the second interface component 48.

Upon the patient or other individual releasing of the first interface component 40 from the second interface component 48, as shown in FIG. 5B, the ball 22 rolls into the opening of the first interface component 40 to seal the opening thereto from contaminants and the like. The ball 22 has a diameter larger than the opening of the first interface component 40 resulting in the opening being sealed.

Figure 6A:
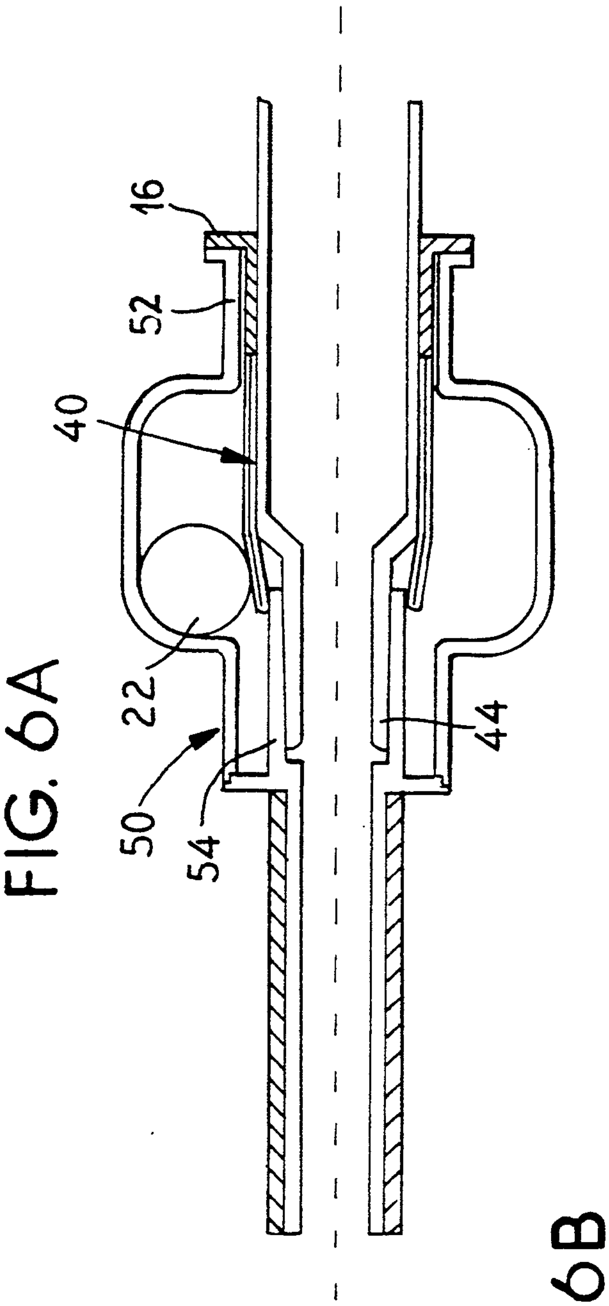
FIG. 6A illustrates a cross-sectional view of a connector and an interface in another embodiment of the present invention in a non-occluded position.
Figure 6B:
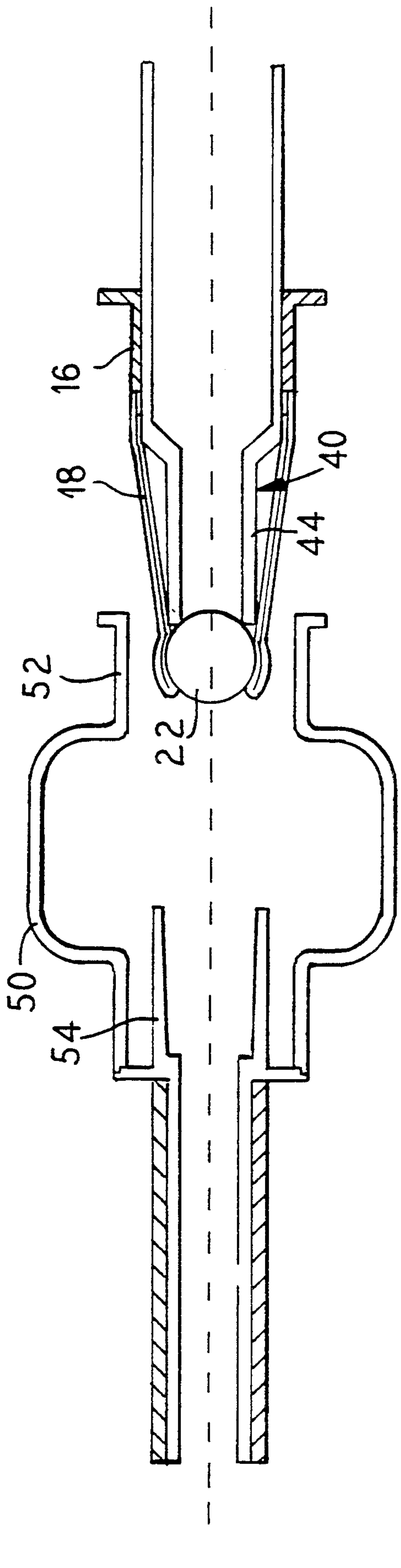
FIG. 6B illustrates a cross-sectional view of the embodiment shown in FIG. 6A in the occluded position.

Another embodiment of an interface connector is shown in FIGS. 6A and 6B using the connector 16 of the present invention. The first interface component 40 described with reference to FIGS. 5A and 5B may be implemented with the interface illustrated in FIGS. 6A and 6B. To this end, a single chamber interfacing connector 50 is provided having a receiving end 52 for receiving the connector 16 and the first interface component 40. The interfacing connector 50, in the position shown in FIG. 6A, provides fluid communication between a source and a fluid line, such as a fluid line to a patient. The ball 22 is secured in a sterile manner within the interfacing connector 50 as shown. An interior receiving portion 54 receives the exterior wall 44 of the first interface component 40.

Referring to FIG. 6B, the release of the connector 16 by the patient or user from the interior of the interfacing connector 50 allows the ball 22 to transpose into the opening at the end of the first interface component 40. The transposition of the ball 22 into the opening at an end of the first interface component 40 initiates upon release from the receiving portion 54 such that a sealed relationship is effected prior to removal of the connector 16 from the interfacing connector 50. In this manner, a substantially sterile, contaminant-free relationship is maintained for the system.

Figures 7A, 7B, 7C:
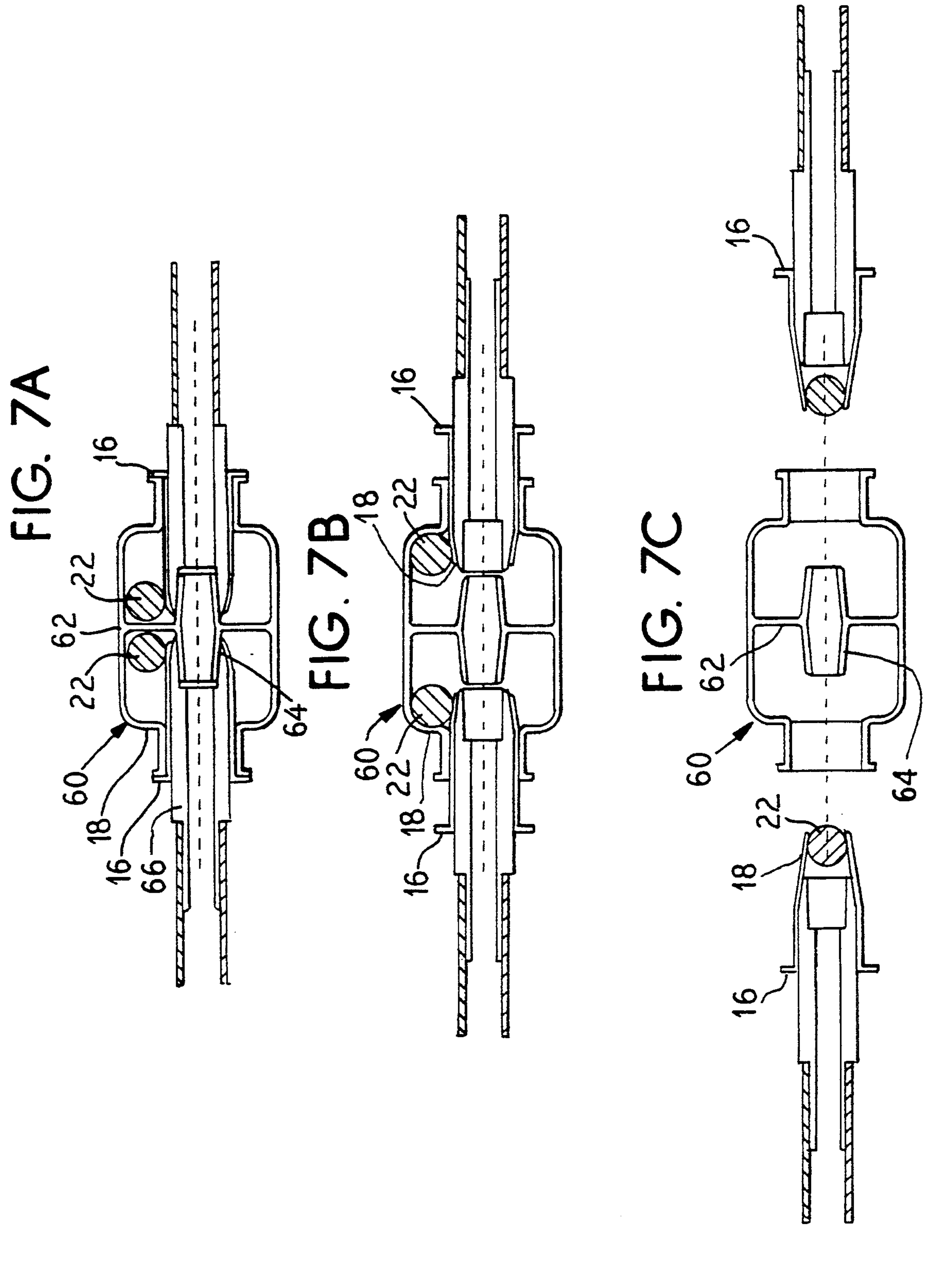
FIG. 7A illustrates a cross-sectional view of a pair of connectors and an interface in a non-occluded or connected position in another embodiment of the present invention.
FIG. 7B illustrates a cross-sectional view of the embodiment of the present invention shown in FIG. 7A in the start of disconnect.
FIG. 7C illustrates a cross-sectional view of the embodiment of the present invention shown in FIGS. 7A and 7B in a disconnected or occluded position.

Another embodiment of a dual chamber interfacing connector 60 is shown in FIGS. 7A, 7B and 7C. FIG. 7A illustrates a "connected mode" in which fluid communication is effected between a source and a fluid line leading to a patient. Two connectors 16 of the present invention each having a ball 22 are provided for connection within the interfacing connector 60. An interior wall 62 divides the interfacing connector 60 into substantially two equal receiving chambers for the connectors 16 with their respective balls 22 and tubings 18.

The interior wall 62 within the interfacing connector 60 forms a receiving portion 64 to the interior of the interfacing connector 60. The receiving portion 64 in the interior of the interfacing component 66 receives the connector 16. The tubing 18 with the integrally formed ball 22 extends from the connector 16. The interfacing connector 60 thereby provides a sterile environment for the flow of a fluid or a solution between a container and a fluid line.

FIG. 7B illustrates the start of the disconnect mode of FIG. 7 and for interrupt. Further, one connector 16 or both of the connectors 16 may be disconnected in a "disconnected mode" from the interfacing connector 60 as shown in FIG. 7C. Withdrawal of either or both of the connectors 16 by the patient or other individual may be continued from the position illustrated in FIG. 7B such that the integrally formed ball 22 with the interface 18 of the connector 16 transposes to seal the openings of the interface 18 from the connectors 16 as previously discussed in the other embodiments.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A connector for controlling fluid communication in a fluid path between a first fluid line and a second fluid line, the connector comprising:

a flange;

a tube, defining in part the first fluid line, having an interior surface and an exterior surface wherein the tube extends through the flange and is located so as to expose a portion of the interior surface of the tube by a portion of the tube being folded over a portion of the flange; and an occluder coupled to the interior surface of the tube and integrally formed with the interior surface of the tube wherein the occluder is so constructed and arranged to transpose between a first position and a second position in response to movement of the flange.

2. The connector of claim 1 wherein the flange has a first end and a second end wherein the first end has a larger exterior diameter than the second end.

3. The connector of claim 1 wherein the second position of the occluder seals an end of the tube.

4. The connector of claim 1 wherein the occluder is constructed from silicone.

5. The connector of claim 1 wherein the occluder is spherically shaped.

6. The connector of claim 1 wherein the occluder has a diameter larger than the cross-sectional diameter of the interior surface of the tube.

7. A system for controlling fluid communication between a first fluid line and a second fluid line comprising:

a first tubing, defining at least in part the first fluid line, having an interior surface and an exterior surface;

a first connector for receiving the first tubing, and allowing the first tubing to be coupled to the second fluid line, the first tubing being folded over the first connector exposing a portion of the interior surface of the first tubing;

a first occluder coupled to and integrally formed with the interior surface of the first tubing, the first occluder being so constructed and arranged to selectively transpose between a first position and a second position, in the first position, the occluder covers an opening of the first tubing and in the second position, the occluder does not cover the opening of the first tubing; and means for assisting in transposing the first occluder between the first position and the second position.

8. The system of claim 7 further comprising:

a flange within the first tubing for receiving the means for assisting.

9. The system of claim 8 wherein the first occluder moves to the first position when the flange is removed from the means for assisting and the first occluder moves to the second position when the flange is received in the means for assisting.

10. The system of claim 7 wherein the means for assisting transposes the first occluder from the second position to the first position within an enclosure coupled to the means for assisting.

11. A system for controlling fluid communication between a first fluid line and a second fluid line comprising:

a first tubing, defining at least in part the first fluid line, having an interior surface and an exterior surface;

a first connector for receiving the first tubing, and allowing the first tubing to be coupled to the second fluid line, the first tubing being folded over the first connector exposing a portion of the interior surface of the first tubing;

a first occluder coupled to the interior surface of the first tubing, the first occluder being so constructed and arranged to selectively transpose between a first position and a second position, in the first position, the occluder covers an opening of the first tubing and in the second position, the occluder does not cover the opening of the first tubing;

means for assisting in transposing the first occluder between the first position and the second position;

a second tubing, defining in part the second fluid line, having an interior surface and an exterior surface;

a second connector for receiving a portion of the second tubing wherein a portion of the second tubing is folded over the second connector exposing a portion of the interior surface of the second tubing; and a second occluder coupled to the interior surface of the second tubing wherein the second occluder is so constructed and arranged to selectively transpose between a first position and a second position.

12. The system of claim 11 wherein when the first connector and the second connector are moved away from each other, fluid communication between the two fluid lines is interrupted and the occluders automatically move to the first position.

13. The system of claim 11 wherein at least one of the connectors can be disconnected from the interface such that its respective occluder transposes into its first position.

14. A method for controlling fluid flow between a first fluid line and a second fluid line, the method comprising the steps of:

providing a connector intermediate the first fluid line and the second fluid line;

providing a first length of tubing, defining in part the first fluid line, having an interior through the connector;

folding a portion of the first length of tubing over the connector exposing a portion of the interior of the first length of tubing;

providing an occluder coupled to the interior of the first length of tubing and so constructed and arranged to transpose between a first position and a second position, in the first position, fluid flow is prevented through an opening of the first length of tubing, and in the second position, fluid flow is permitted through the opening in the first length of tubing; and providing means for causing the occluder to move from the first position to the second position.

15. The method of claim 14 further comprising the step of:

providing an enclosure for moving the occluder; and interrupting fluid flow without removal of the connector from the enclosure.

16. The method of claim 14 wherein the occluder is integrally formed with the first length of tubing.

17. The method of claim 15 further comprising the step of:

removing the connector from the enclosure such that the occluder transposes to the first position.

18. The method of claim 14 further comprising the step of:

providing a second length of tubing, defining at least in part the second fluid line, having an interior through a second connector;

folding the second length of tubing over the second connector exposing a portion of the interior of the second length of tubing; and providing a second occluder coupled to the interior of the second length of tubing and so constructed and arranged to transpose between a first position and a second position, in the first position, fluid flow is prevented, and in the second position, fluid flow is permitted.

19. The method of claim 14 wherein the method for controlling fluid flow is used to provide peritoneal dialysis to the patient.

* * * * *